US009861370B2

(12) United States Patent
Clark et al.

(10) Patent No.: US 9,861,370 B2
(45) Date of Patent: Jan. 9, 2018

(54) OCCLUSION DEVICE

(71) Applicant: Boston Scientific Scimed, Inc., Maple Grove, MN (US)

(72) Inventors: Christopher J. Clark, St. Michael, MN (US); Brian Joseph Tischler, New Brighton, MN (US); Dennis A. Peiffer, Brooklyn Park, MN (US); Timothy J. Ley, Shoreview, MN (US); Thyna M. Chau, Oakdale, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 741 days.

(21) Appl. No.: 13/673,452

(22) Filed: Nov. 9, 2012

(65) Prior Publication Data

US 2013/0138138 A1    May 30, 2013

Related U.S. Application Data

(60) Provisional application No. 61/557,681, filed on Nov. 9, 2011.

(51) Int. Cl.
*A61M 29/00* (2006.01)
*A61B 17/12* (2006.01)
*A61B 17/00* (2006.01)

(52) U.S. Cl.
CPC .. *A61B 17/12022* (2013.01); *A61B 17/12172* (2013.01); *A61B 17/12177* (2013.01);
(Continued)

(58) Field of Classification Search
USPC ........................................ 606/200; 623/1.24
See application file for complete search history.

(56) References Cited

U.S. PATENT DOCUMENTS 6,120,534 A    9/2000  Ruiz
6,152,144 A   11/2000  Lesh et al.
(Continued)

FOREIGN PATENT DOCUMENTS

JP     2005515830 A    6/2005
WO       96/14808 A1   5/1996
(Continued)

OTHER PUBLICATIONS

Blackshear et al., "Appendage Obliteration to Reduce Stroke in Cardiac Surgical Patients with Atrial Fibrillation," Ann. Thorac. Surg., 1996; 61(2):755-759.
(Continued)

*Primary Examiner* — Gregory Anderson
*Assistant Examiner* — Sarah Simpson
(74) *Attorney, Agent, or Firm* — Seager, Tufte & Wickhem LLP

(57) ABSTRACT

An occlusion device (e.g., for treatment of the left atrial appendage) includes a framework and a biocompatible covering disposed over at least a part of the framework. The framework may include a proximal portion, a middle portion, and a distal portion, wherein: the proximal portion includes a first hub that has a fixed first diameter; the middle portion has a second diameter and includes a plurality of beams extending from the first hub to a distal portion, wherein each of the plurality of beams is connected to an adjacent beam by a first circumferentially extending column of strut pairs; and the distal portion has a third diameter. In one or more embodiments, the framework includes improved circumferential strength and minimizes foreshortening.

15 Claims, 12 Drawing Sheets

(52) U.S. Cl.
CPC ............... *A61B 17/12122* (2013.01); *A61B 2017/00526* (2013.01); *A61B 2017/00867* (2013.01)

(56) References Cited

U.S. PATENT DOCUMENTS

| | | | |
|---|---|---|---|
| 6,551,303 | B1 | 4/2003 | Van Tassel et al. |
| 6,652,556 | B1 | 11/2003 | VanTassel et al. |
| 6,660,021 | B1 * | 12/2003 | Palmer et al. ............... 606/200 |
| 6,689,150 | B1 | 2/2004 | VanTassel et al. |
| 6,989,021 | B2 * | 1/2006 | Bosma et al. ............... 606/200 |
| 6,994,092 | B2 | 2/2006 | van der Burg et al. |
| 7,727,189 | B2 | 6/2010 | VanTassel et al. |
| 8,114,147 | B2 | 2/2012 | Wood et al. |
| 2005/0015111 | A1 * | 1/2005 | McGuckin et al. .......... 606/200 |
| 2007/0021826 | A1 * | 1/2007 | Case et al. ................. 623/1.15 |
| 2010/0063533 | A1 * | 3/2010 | Sokolov et al. ............. 606/200 |
| 2010/0228281 | A1 * | 9/2010 | Gilson et al. ................ 606/200 |
| 2011/0054515 | A1 | 3/2011 | Bridgeman et al. |
| 2012/0239083 | A1 | 9/2012 | Kreidler |

FOREIGN PATENT DOCUMENTS

| | | |
|---|---|---|
| WO | 97/25937 A1 | 7/1997 |
| WO | 01/06954 A1 | 2/2001 |
| WO | 2004/016199 A1 | 2/2004 |

OTHER PUBLICATIONS

International Search Report and Written Opinion of the International Searching Authority, International Application No. PCT/US2012/064461 (Filing Date: Nov. 9, 2012), mailed Jan. 30, 2013, 12 pgs.

* cited by examiner

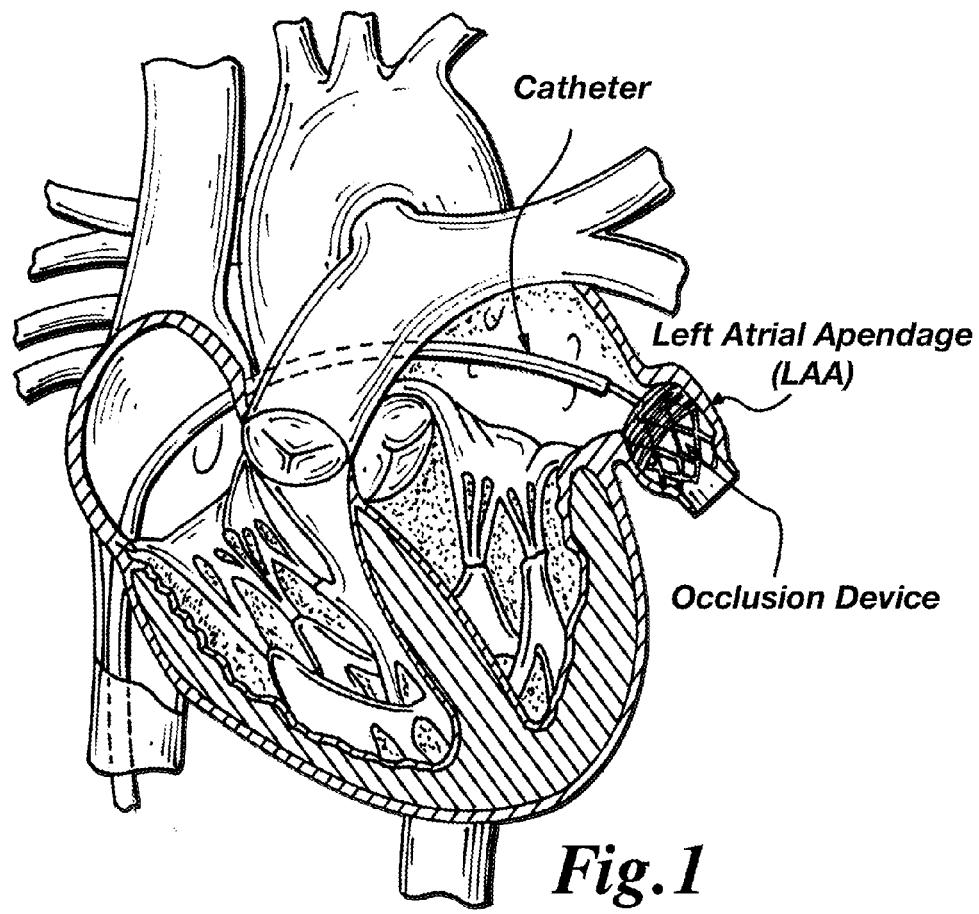
Fig.1
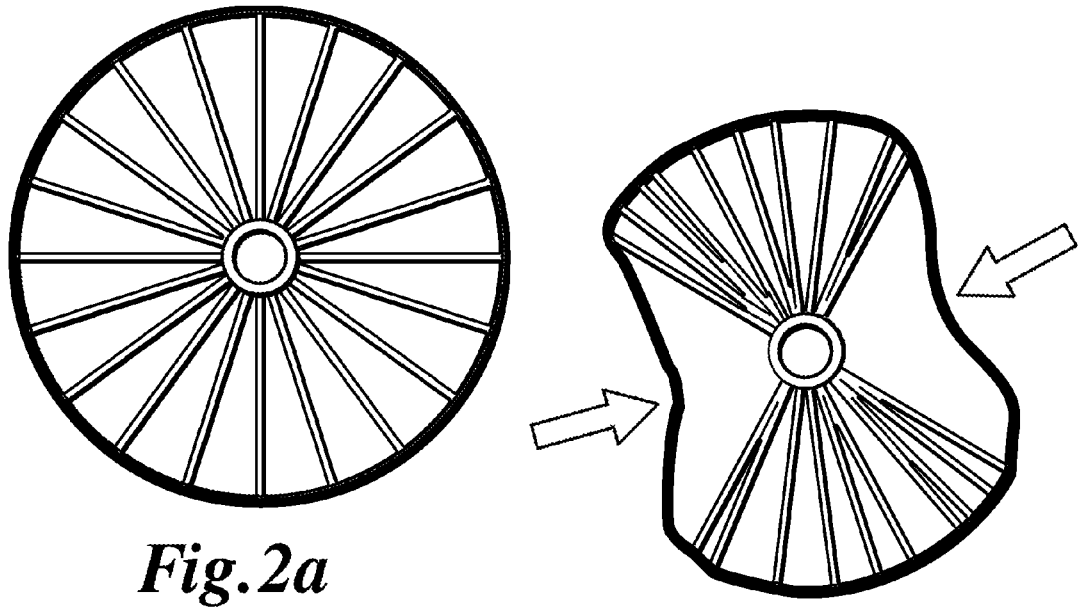
Fig.2a
(PRIOR ART)
Fig.2B
(PRIOR ART)

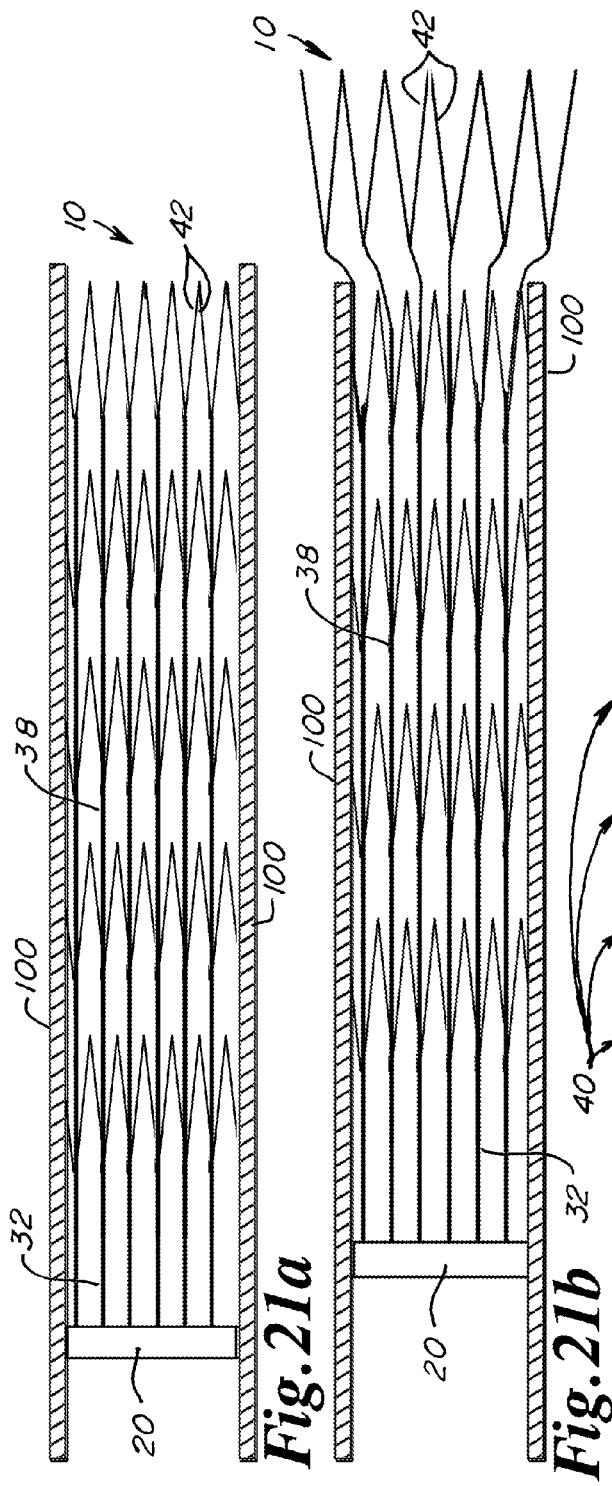

OCCLUSION DEVICE

CROSS-REFERENCE TO RELATED APPLICATIONS

This application claims the benefit of U.S. patent application Ser. No. 61/557,681, filed Nov. 9, 2011, the entire contents of which is hereby incorporated by reference.

BACKGROUND

The present disclosure relates to methods and devices for occluding a body lumen. For example, at least one embodiment is directed to a device and method for occluding the left atrial appendage of the heart.

Atrial fibrillation (AF) is the most common sustained cardiac arrhythmia affecting over 5.5 million people worldwide. AF is the irregular, chaotic beating of the upper chambers of the heart. Electrical impulses discharge so rapidly that the atrial muscle quivers or fibrillates. Episodes of AF may last a few minutes or several days. A serious consequence of AF is ischemic stroke. It is estimated that up to 20% of all strokes are related to AF. Most AF patients, regardless of the severity of their symptoms or frequency of episodes, require treatment to reduce the risk of stroke. In patients with AF, blood tends to pool and form clots in an area of the heart called the left atrial appendage (LAA). The LAA is a pouch-like extension located in the upper left chamber of the heart. A blood clot that breaks loose from this area may migrate through the blood vessels and eventually plug a smaller vessel in the brain or heart resulting in a stroke or heart attack. Clinical studies show that the majority of blood clots in patients with AF are found in the LAA (see Blackshear J. L., Odell J. A., Appendage Obliteration to Reduce Stroke in Cardiac Surgical Patients with Atrial Fibrillation. Annals of Thoracic Surgery, 1996;61:755-759).

Treatment of AF may include surgically closing the LAA, epicardial LAA ligation, or delivering a device or mechanism across or into the LAA in order to occlude it. Occlusion devices for addressing AF typically utilize a metallic "cage" and/or fabric graft, which, when deployed, form a circular shape across and/or within the LAA. They are delivered to the treatment site via a catheter system (see, e.g., U.S. Pat. No. 6,994,092 to van der Burg et al.; U.S. Pat. Nos. 6,652,556 and 7,727,189 to Van Tassel et al., the entire contents of all of which are incorporated herein by reference).

In FIG. 1, a cross-sectional view of the human heart is shown. FIG. 1 also depicts a common technique whereby a catheter is threaded through the vasculature and into the heart to deliver an occlusion device to the LAA. Ideally, when the device is properly positioned within the LAA the occlusion device forms a seal with the wall of the LAA in order to prevent emboli or blood clots from passing back into the blood stream. Many known occlusion devices (an example of which is shown in PRIOR ART FIG. 2a), however, are equipped with frameworks that while sufficient to support a filter or membrane, have insufficient circumferential and/or radial strength to resist the distortive forces (indicated by arrows in PRIOR ART FIG. 2b) that the LAA exert on the occlusion device. As a result, the seal such devices form with the interior wall of the LAA is compromised as the framework is bent into a more elliptical shape by the LAA. As a consequence, such devices may allow some material to exit the LAA and re-enter the blood stream.

Even where such known occlusion devices maintain their seal despite being distorted, the irregularity of the device's shape can also result in flattening during recapture of the device into the delivery catheter.

Many occlusion devices may suffer from effects of foreshortening. Foreshortening during expansion of expandable occlusion devices may negatively affect deployment accuracy. For example, an expandable occlusion device that foreshortens during expansion may tend to be more difficult to deploy since the position of the distal end of the device changes by shrinking back toward the proximal end as the device expands (i.e., the longitudinal distance between the distal end and proximal end shortens upon expansion). Deployment accuracy may be improved by reducing or eliminating foreshortening.

As such, there remains a need for an occlusion device that has improved circumferential strength without foreshortening or excessive distortion.

The above reference to and/or description of documents is not intended to constitute an admission that any patent, publication, or other information referred to herein is "prior art" with respect to this disclosure. In addition, this section should not be construed to mean that a search has been made or that no other pertinent information as defined in 37 C.F.R. §1.56(a) exists.

BRIEF SUMMARY

One or more occlusion devices and treatment methods described herein include a framework design that may provide improved circumferential strength, while maintaining flexibility, deliverability, and ease of recapture of the device. In some embodiments, the framework may evenly control the stability of the longitudinally extending beams by providing a supportive but flexible column of strut pairs between each beam (e.g., support beam).

In one or more embodiments of the present disclosure, an occlusion device may include, among other things, a framework including a proximal portion, a middle portion, and a distal portion; and a biocompatible covering (e.g., graft and/or a membrane) disposed over at least a part of the framework. The proximal portion of the framework may include a first hub (e.g., a cap or ring) that has a fixed first diameter. In one or more embodiments, the middle portion of the framework may have a second diameter and may include a plurality of beams extending from the first hub to a distal portion, wherein each of the plurality of beams may be connected to an adjacent beam by a first circumferentially extending column of strut pairs. The distal portion of the framework may have a third diameter. In one or more embodiments, the distal portion includes a second hub (e.g., a cap or ring). One or both of the first and second hubs may be inverted, which may result in J-shaped or C-shaped beams.

In one or more embodiments, the middle portion of the framework may be movable between a first configuration wherein the second diameter is not greater than the first diameter and a second configuration wherein the second diameter is greater than the first diameter. The middle portion may or may not include an anchor extending from the middle portion (e.g., through a covering).

In one or more of the frameworks described herein, each of the plurality of beams may be connected to an adjacent beam by a second circumferentially extending column of strut pairs. Each beam may include, among other things, a first segment extending from the first hub to the first circumferentially extending column of strut pairs and a second segment extending from the first circumferentially extending column of strut pairs to the second circumferentially extending column of strut pairs. In one or more embodiments a strut pair may or may not have the same length as another strut pair. In one or more embodiments, upon moving from the first configuration to the second configuration, there is substantially no foreshortening of the second segment. An occlusion device of the present disclosure may include a third circumferentially extending column of strut pairs connecting the first segments and disposed between the first circumferentially extending column of strut pairs and the first hub.

BRIEF DESCRIPTION OF THE SEVERAL VIEWS OF THE DRAWING(S)

A detailed description is hereafter provided with specific reference being made to the drawings.

FIG. 1 is a cross-sectional illustration of the human heart depicting the left atrial appendage (LAA) and a mode of access by a catheter assembly through which one or more embodiments of the present disclosure may be deployed.

FIG. 2a is a schematic representation of a PRIOR ART occlusion device having insufficient circumferential support shown in an expanded state, but prior to deployment in the LAA.

FIG. 2b is an illustration of how the forces within the LAA can affect the PRIOR ART occlusion device shown in FIG. 2a when deployed within the LAA.

Figure 3:
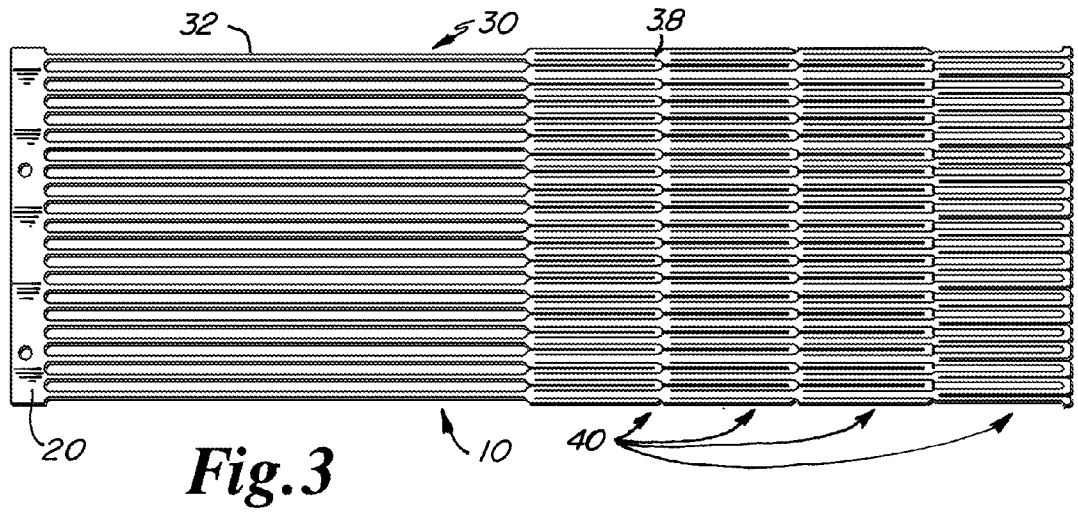
FIG. 3 is a flat side view of one or more embodiments of the framework of the present disclosure shown in a manufactured state (prior to insertion into a catheter delivery system and deployment).

FIGS. 21a, 21b, and 21c are schematic side views of one or more embodiments of an occlusion device of the present disclosure coupled with a delivery mechanism going through the process of delivery while compressed within a delivery device (FIG. 21a), partial deployment of an occlusion device (FIG. 21b), and expanded, deployed configuration of the occlusion device with the delivery device removed (FIG. 21c).

DETAILED DESCRIPTION

While the subject matter of the present disclosure may be embodied in many different forms, there are described in detail herein specific embodiments. This description is an exemplification of the principles of the present disclosure and is not intended to be limited to the particular embodiments illustrated.

For the purposes of this disclosure, like reference numerals in the figures shall refer to like features unless otherwise indicated. For example, reference numeral 10 refers to a framework in FIG. 4 and also refers to a framework in FIG. 5.

In one or more aspects of the present disclosure, an occlusion device may include a framework and a biocompatible covering disposed over at least a part of the framework. An occlusion device of the present disclosure may be used to, for example, occlude the left atrial appendage (LAA) of the heart for the treatment of, for example, sustained cardiac arrhythmia (e.g., atrial fibrillation). When an occlusion device of the present disclosure is properly positioned within the LAA, the occlusion device may have sufficient circumferential and/or radial strength form a seal with the wall of the LAA (and resist the distortive forces that the LAA may exert on the occlusion device) in order to, for example, prevent emboli or blood clots from passing back into the blood stream.

With reference to FIG. 3, an occlusion device may include a framework 10 formed from, for example, a sheet. The framework 10 may be suitable for use as a component of an occlusion device, which may also include covering (e.g., a filter graft, membrane, etc.). Such a covering may be supported by the framework 10 (e.g., the covering may extend over and from the proximal end of the framework toward the distal end of the framework). The occlusion device (including the framework and covering) may include other components, and may be combined with a delivery system for delivering the occlusion device to the LAA or other body lumen. In the one or more embodiments shown in FIG. 3, the framework 10 is depicted after manufacture, but before being loaded onto a catheter or deployed.

Figure 4:
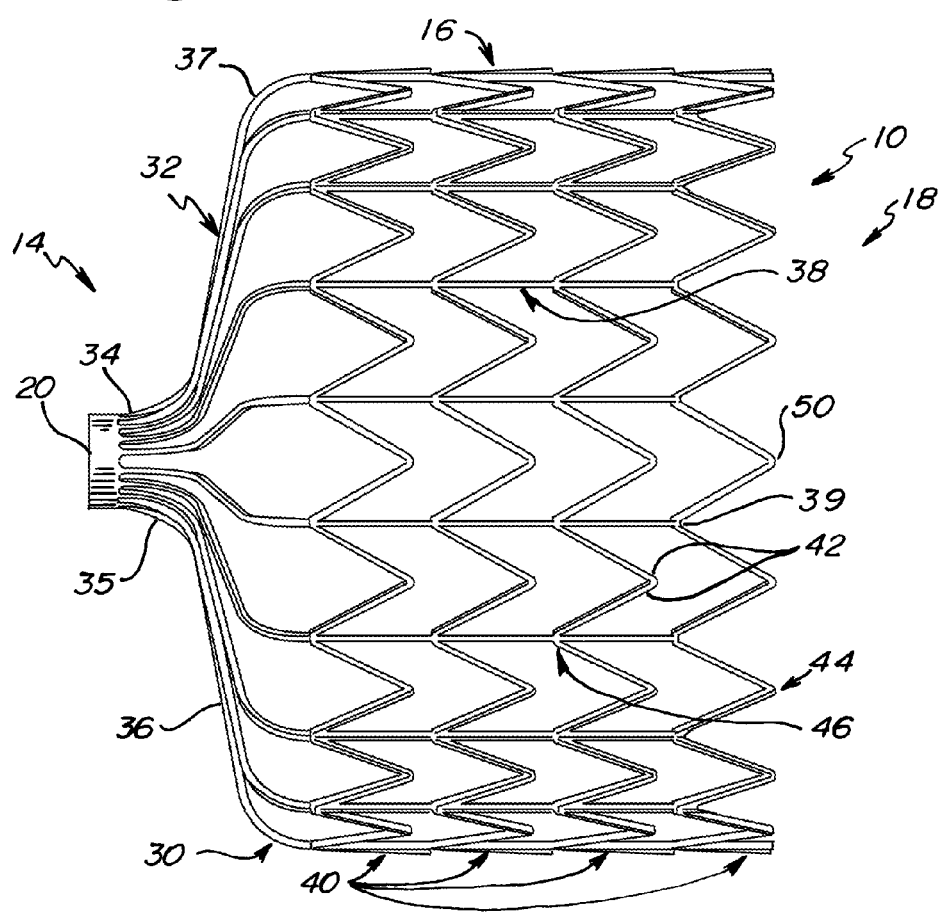
FIG. 4 is a side view of one or more embodiments of the framework shown in FIG. 3 shown in an expanded state.
Figure 5:
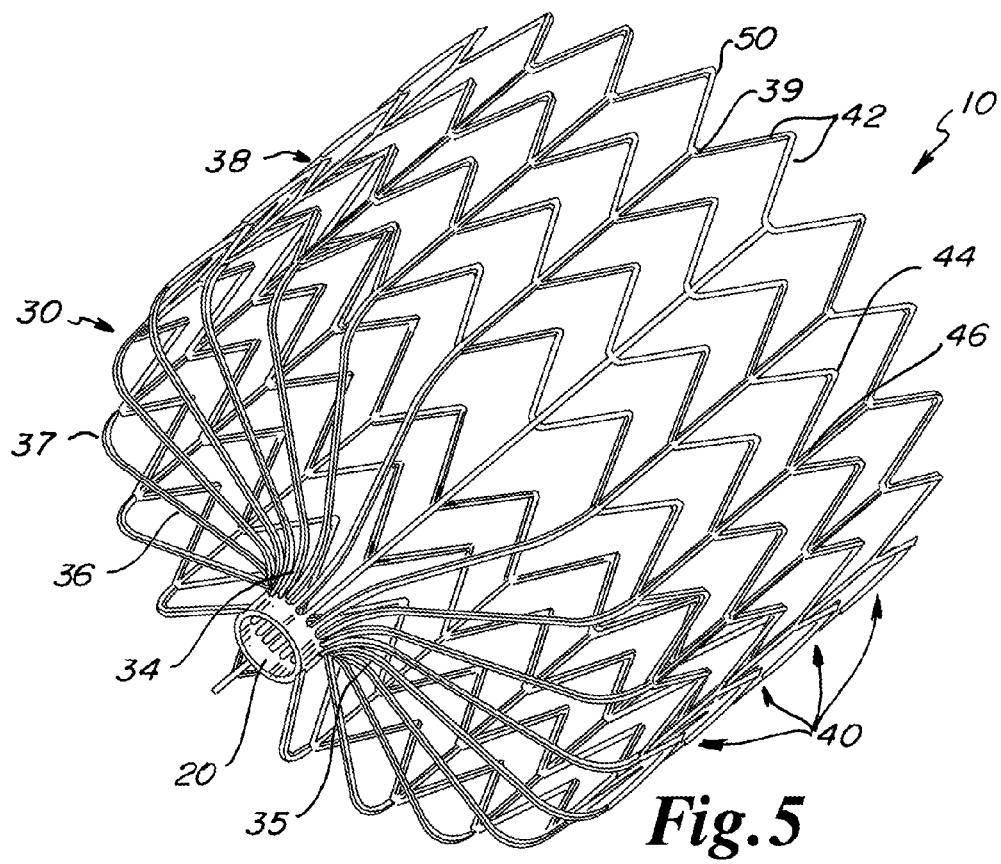
FIG. 5 is a rear (proximal end) perspective view of one or more embodiments of the framework shown in FIG. 4.
Figure 6:
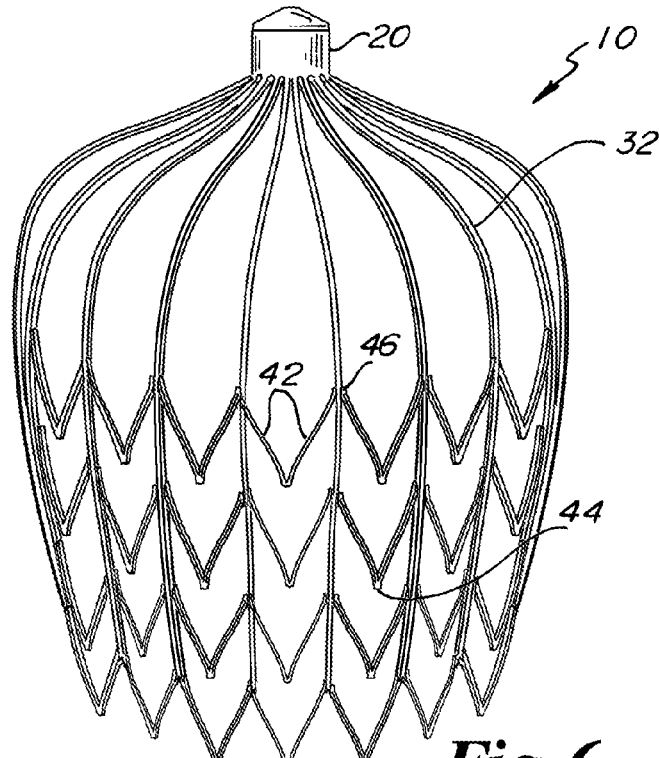
FIG. 6 is a side perspective view of one or more embodiments of the framework shown in FIG. 4
Figure 7:
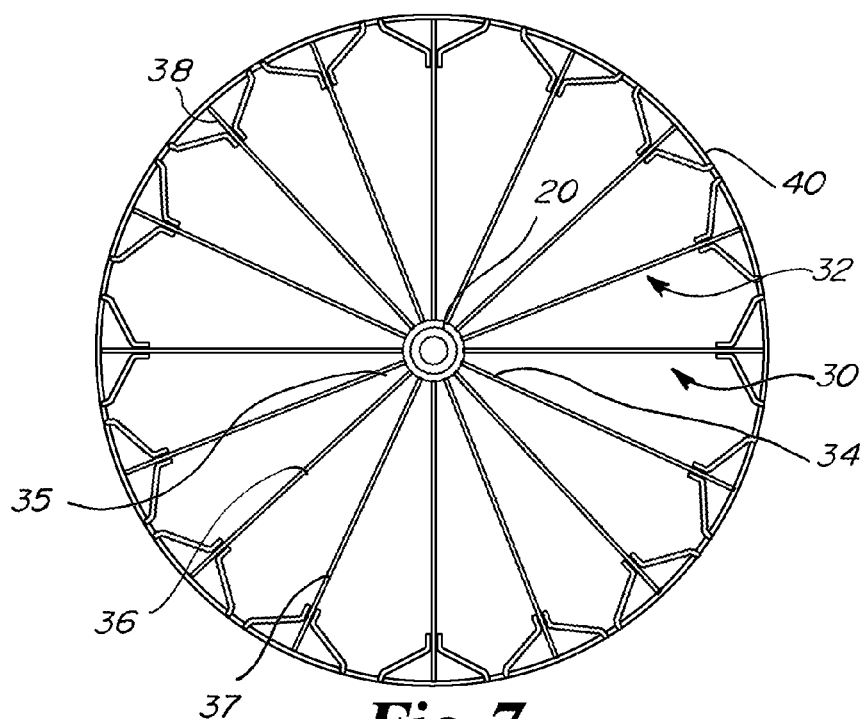
FIG. 7 is a proximal perspective end view of one or more embodiments of the framework shown in FIG. 4.

With reference to FIG. 4, framework 10 may include a proximal portion 14, a middle portion 16, and a distal portion 18. In one or more embodiments, the proximal portion 14 includes a first hub 20 that has a fixed first diameter. In one or more embodiments, the middle portion 16 may have a second diameter and may include a plurality of beams 30 extending from the first hub 20 to the distal portion 18 that has a third diameter. Each of the plurality of beams 30 may be connected to an adjacent beam 30 by a first circumferentially extending column 40 of strut pairs 42.

Framework 10 of FIG. 4 may be formed by rolling the framework 10 of FIG. 3 such that the first hub 20 may include or take the form of a cap or ring and by separating the support beams 30 (extending from the first hub) from each other by, for example, bending the strut pairs 42 to increase the angle formed therebetween. A framework of the present disclosure may include at least one circumferentially extending column 40 (e.g., four columns shown in FIG. 3).

Before the support beams are separated from one another, a framework 10 in the form of a sheet, such as the sheet shown in FIG. 3, may be rolled into a tubular shape (e.g., cylindrical shape), thereby forming a first configuration wherein the second diameter (of the middle portion) is not greater than the first diameter (of the first hub). In one or more embodiments, the middle portion 16 of the framework 10 is movable between the first configuration wherein the second diameter (of the middle portion 16) is not greater than the first diameter (of the first hub 20) and a second configuration (e.g., shown in FIG. 4) wherein the second diameter (of the middle portion 16) is greater than the first diameter (of the first hub 20).

The occlusion devices of the present disclosure are not limited to including only one circumferentially extending column of strut pairs. For example, an occlusion device may include a framework wherein each of the plurality of beams is connected to an adjacent beam by a second circumferentially extending column of strut pairs. Any suitable number of additional columns of strut pairs may be included in the framework. For example, in FIG. 4, framework 10 includes first, second, third, and fourth circumferentially extending columns 40 of strut pairs 42, each column connecting the plurality of beams 30.

As shown in FIG. 4, each strut pair forms a peak 44 and a valley 46. Each valley 46 of every column 40 intersects with a region of the second segment 38 (e.g., longitudinal portion) of the beam 30. Each peak 44 of each strut pair 42 is free from engagement with the beams 30. In one or more of the embodiments shown, the peaks 44 of the distal-most column 40 of strut pairs 42 may define the distal end 50 (FIG. 5) of the framework 10.

In the present disclosure, a beam 30 of framework 10 may include a number of segments. For example, as shown in FIG. 4, each beam 30 may include a first segment 32 extending from the first hub 20 to the first circumferentially extending column 40 of strut pairs 42 and a second segment 38 extending from the first circumferentially extending column 40 of strut pairs 42 to another (e.g., a second, third, fourth, etc.) circumferentially extending column 40 of strut pairs 42.

As can be seen in FIG. 3, the framework 10 includes a first hub 20 (e.g., a proximal cap or ring) from which a plurality of beams 30 (e.g., support beams) extend longitudinally therefrom. The first segment 32 (e.g., the proximal portion) of each beam 30 may also be considered as a radial component of the beam 30 because when the framework 10 is expanded, such as in the manner shown in FIGS. 4-7, the predominant length of the first segment 32 may extend radially outward from first hub 20.

As shown in the one or more embodiments of FIG. 4, the first segment 32 of the beam 30 may include a first longitudinally extending region 34 that is immediately adjacent to the first hub 20. In FIG. 4, the first longitudinal extending region 34 may transition to the radially extending region 36 at interior curve 35. In one or more embodiments, the radially extending region 36 may then transition or turn back to the longitudinal direction at exterior curve 37.

In the one or more embodiments shown in FIGS. 4-7, the second segment 38 (e.g., longitudinal portion) of the beam 30 extends in the longitudinal direction (e.g., entirely in the longitudinal direction). Each beam 30 has a distal end 39 that may terminate in a valley 46 of a strut pair 42.

As shown in FIG. 4, exterior curve 37 extends to a first circumferentially extending column 40 of strut pairs 42, from which the second segment 38 extends in the longitudinal direction.

As shown in FIG. 4, a second segment 38 may extend from a first circumferentially extending column 40 of strut pairs 42 to more than one other circumferentially extending column 40 of strut pairs 42.

In one or more embodiments, upon moving from the first configuration to the second configuration, there is substantially no foreshortening of the second segment 38. For example, this may be seen in FIG. 4, wherein second segment 38 extends from exterior curve 37 to distal end 39 in a manner such that moving from a first configuration to a second configuration does not result in foreshortening of the second segment 38. In one or more embodiments, second segment 38 may be a straight segment of beam 30 or may otherwise be resistant to lengthening (e.g., as a result of moving from the first configuration to the second configuration).

As can be recognized in a comparison of FIGS. 3 and 4, the framework, when moved from a first configuration to a second configuration may experience foreshortening in the first segment 32, in that the longitudinal distance from the first hub 20 to the second segment is significantly shorter in FIG. 4 (e.g., second configuration) than in FIG. 3, due to the radially extending region 36.

In one or more embodiments, it may be useful for a column to include at least two strut pairs having the same length. In some embodiments, all of the strut pairs 42 of a particular column 40 may have the same length. In one or more occlusion devices of the present disclosure, a framework 10 may include columns 40 of strut pairs 42 wherein the strut pairs for a particular column 40 have a different length relative to the strut pairs of a different column. In one or more embodiments, all of the columns 40 of strut pairs 42 connecting second segments have strut pairs that have uniform length and strength. The length of a strut pair is measured when the opening angle between the strut pairs is zero degrees (e.g., in the state depicted in FIG. 3, before strut pair opening). In one or more embodiments, the length of struts further from the longitudinal axis (when viewed in the second configuration or expanded or deployed state) is increased relative to struts closer to the longitudinal axis. In at least one embodiment, the opening angle of the strut pairs is substantially uniform for a particular column or for all columns connecting second segments. In at least one embodiment, the opening angle of at least some strut pairs is different than the opening angle of at least some other strut pairs in a particular column or in a different column connecting second segments.

Figure 8:
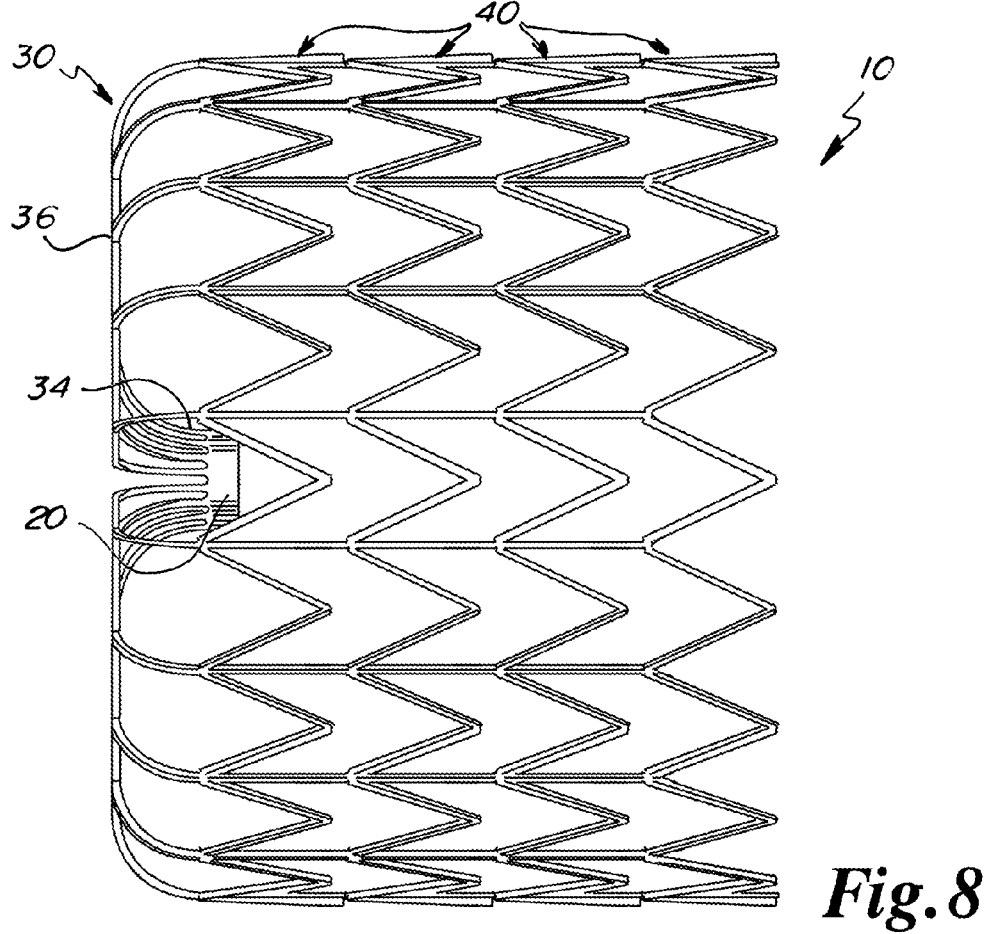
FIG. 8 is a side view of one or more embodiments of the framework shown in FIG. 4 wherein the proximal ring is inverted.
Figure 9:
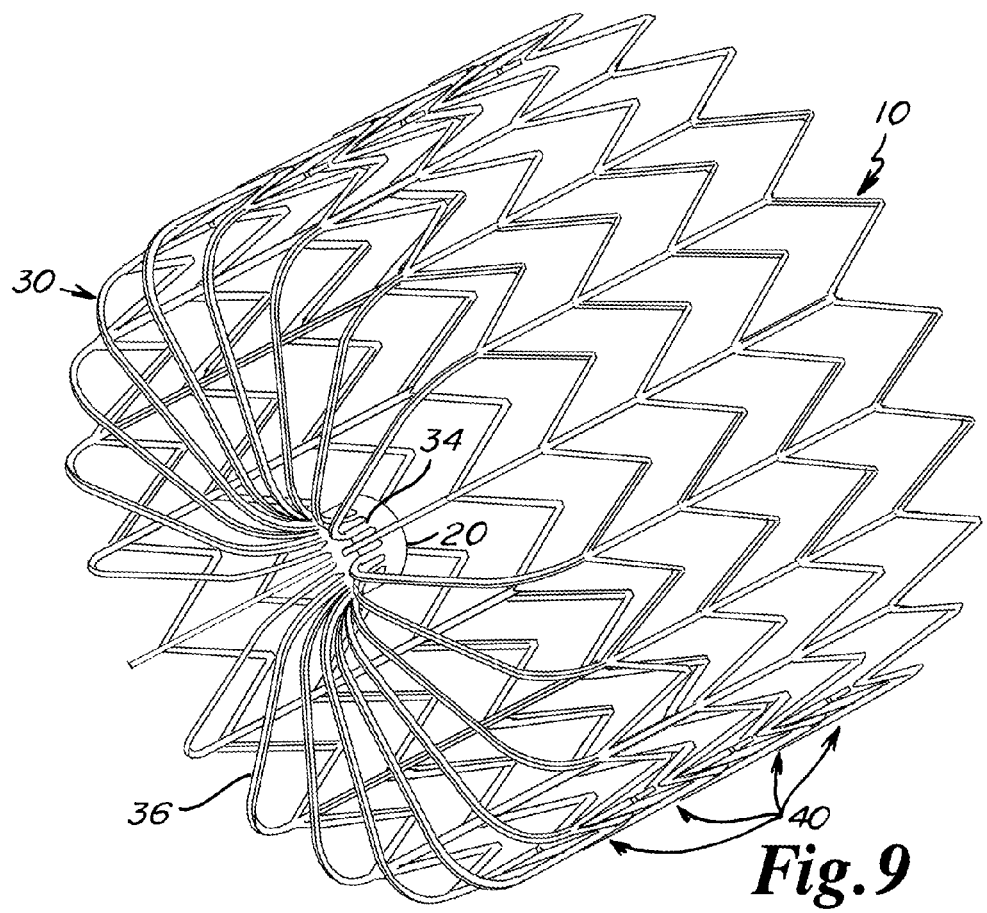
FIG. 9 is a rear (proximal end) perspective view of one or more embodiments of the framework shown in FIG. 8.

As indicated above, in some embodiments, the first hub 20 may be positioned external of the beams 30, such as is shown in the embodiment depicted in FIGS. 4-7 or the first hub 20 may be internal or "inverted" relative thereto. An example of the inverted position of the first hub 20 is shown in FIGS. 8 and 9. As can be seen in these embodiments, the first longitudinally extending region 34 of the beam 30 extends longitudinally away from the first hub 20 in a proximal direction, rather than in the distal direction that is shown in FIGS. 4-7. The interior positioning of the first hub 20 results in the radially extending portion 36 of the beams defining the proximal end of the framework 10. The remaining structure of the beams 30 and strut columns 40 may be the same as described with respect to FIGS. 4-7.

With reference to FIGS. 10-13, one or more embodiments of the present disclosure may include a framework 10 including an anchor 60. For example, the framework may include one or more radially extending anchors (e.g., engagement barbs or other features) for improved securement of the framework into the surrounding tissue (e.g., the interior wall of the LAA) when the device is deployed.

Figure 11:
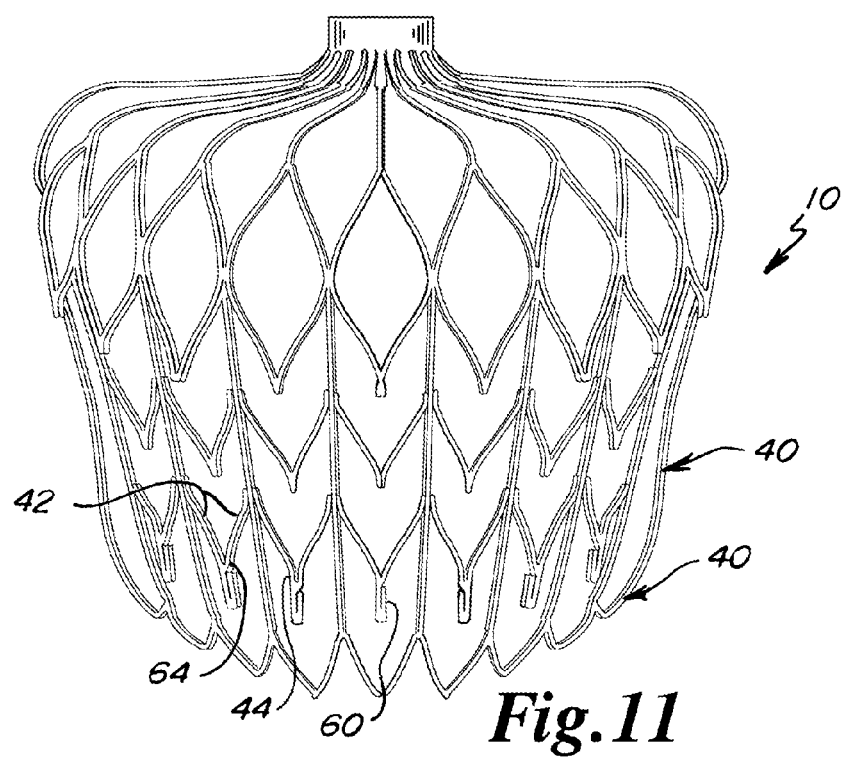
FIG. 11 is a side perspective view of one or more embodiments of the framework shown in FIG. 10 in an expanded state.
Figure 10:
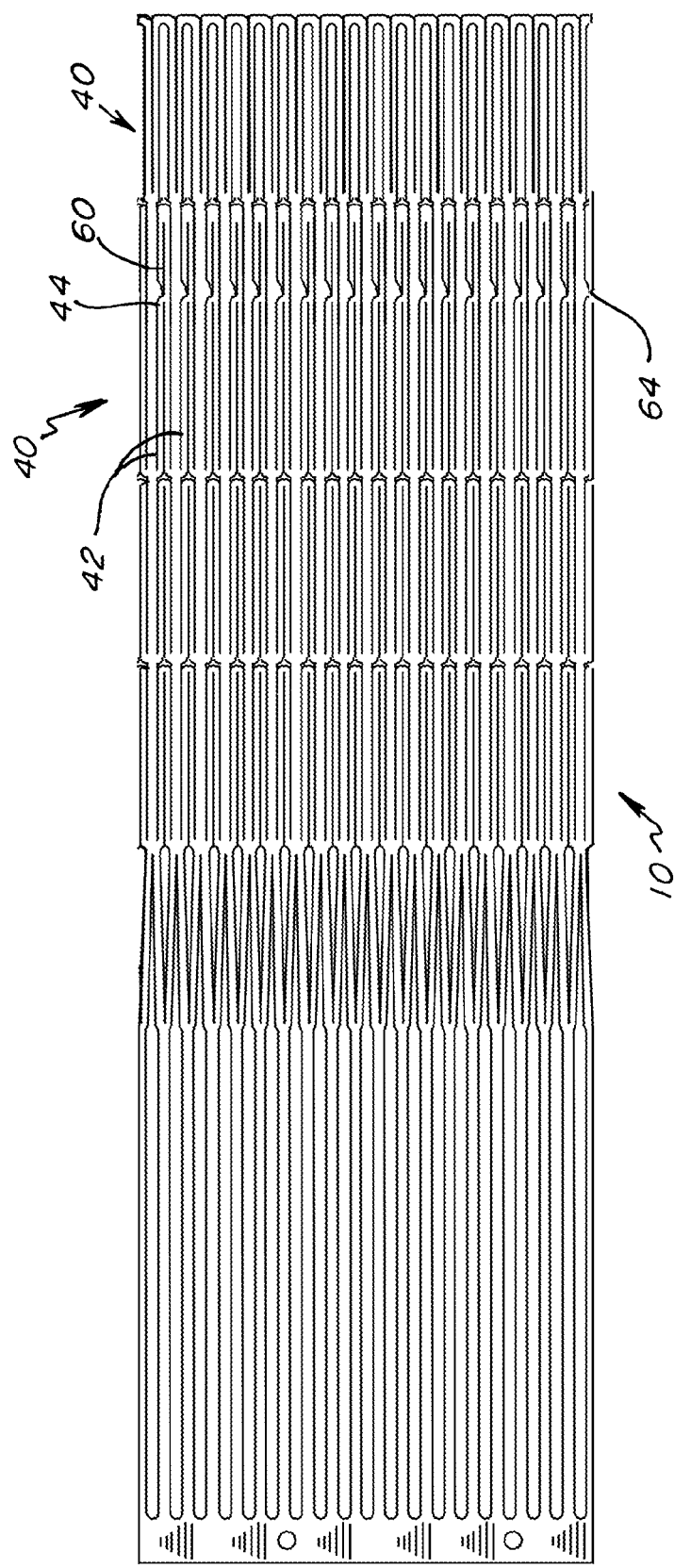
FIG. 10 is a flat side view of one or more embodiments of a framework of the present disclosure having securement anchors as shown in the manufactured state (prior to insertion into a catheter delivery system and deployment).
Figure 12:
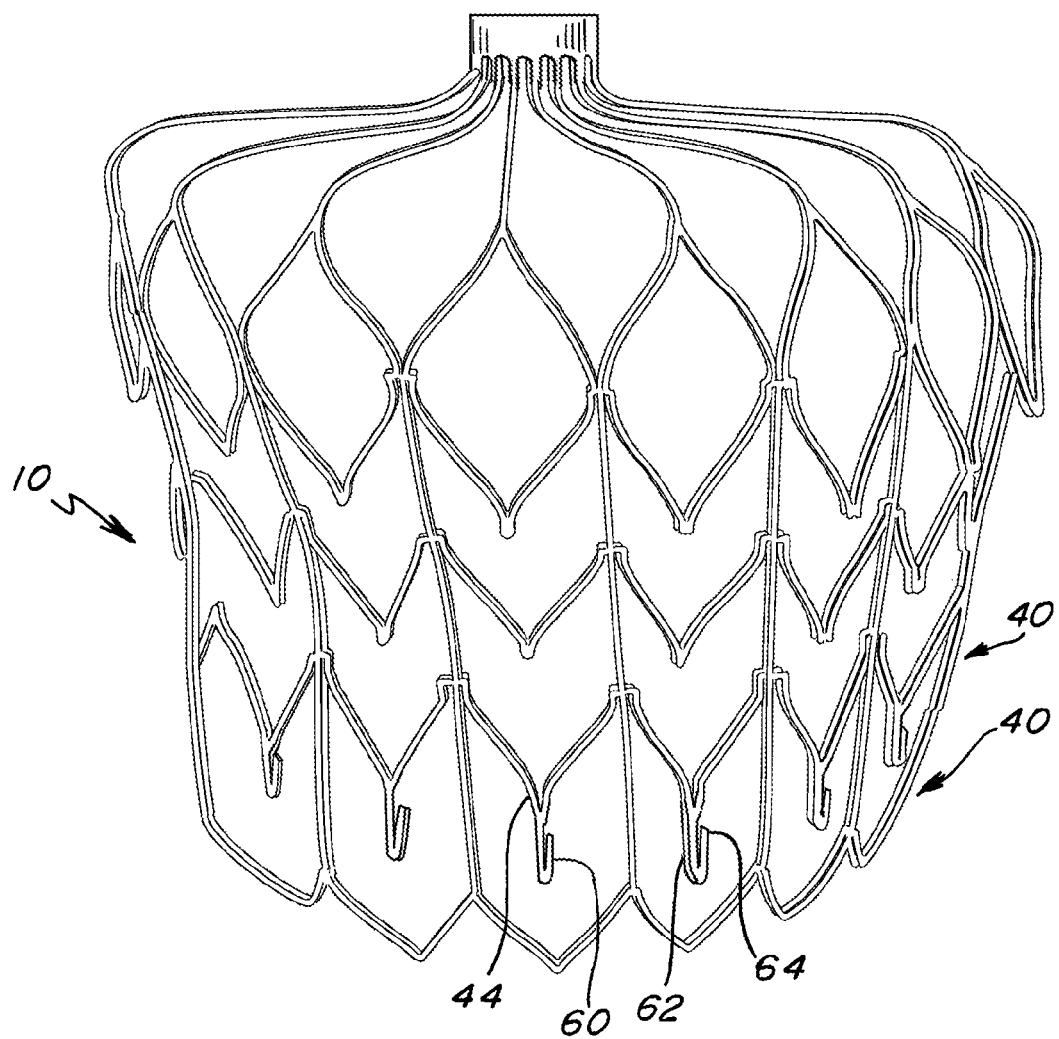
FIG. 12 is an enlarged view of one or more embodiments of the framework shown in FIG. 11.
Figure 13:
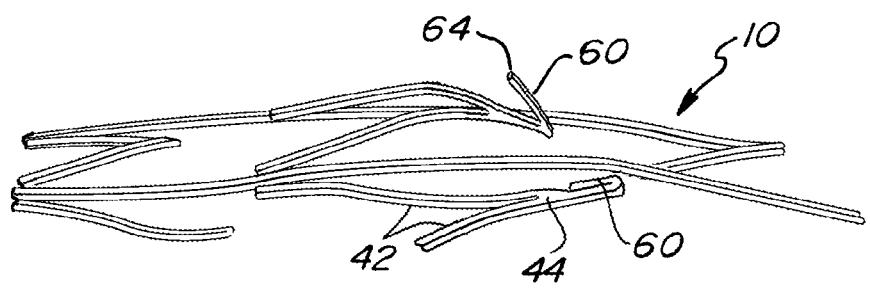
FIG. 13 is a close-up view of one or more embodiments of the securement anchor present in FIGS. 10-12 shown in a deployed or engaged configuration.

Anchors 60 may be distributed about the surface of the framework 10 in any manner desired. In one or more embodiments, such as are depicted in FIGS. 10-12, a plurality of anchors 60 are positioned along a column 40 of strut pairs 42. As shown, the peak 44 of each strut pair 42 in the selected column may include a single anchor 60. In the one or more embodiments shown, each anchor 60 may include an anchor strut 62 (FIG. 12) that extends distally away from the peak 44, but which may turn back proximally toward the originating peak and terminate adjacent thereto. The end of the anchor 60 may be notched or angled to form an engagement surface 64. When the framework 10 is deployed the engagement surface 64 may flare circumferentially outward and/or radially outward from the peak 44 (such as in the manner shown in FIG. 13) to engage the surrounding tissue (e.g., a wall of the LAA).

In embodiments in which the framework 10 is equipped with anchors 60, the framework 10 and anchors 60 may have any structural characteristics, such as those described herein. In at least one embodiment, the anchors may be positioned on the framework 10 such that there is at least one column 40 of strut pairs 42 proximal of the anchor(s) 60 and one column 40 of strut pairs 42 distal of (e.g., distally adjacent to) the anchor(s) 60. For example, an anchor 60 may extend from the middle portion 16 of framework 10 and may extend through a covering disposed on the framework. Anchors 60 may include a shorter beam that may run parallel to the other beams 30, but may curve radially inward toward the center of the framework 10, and then back radially outward beyond the circumference defined by the beams 30. Anchors may take any of a wide variety of shapes known to one of skill in the art.

Figure 14:
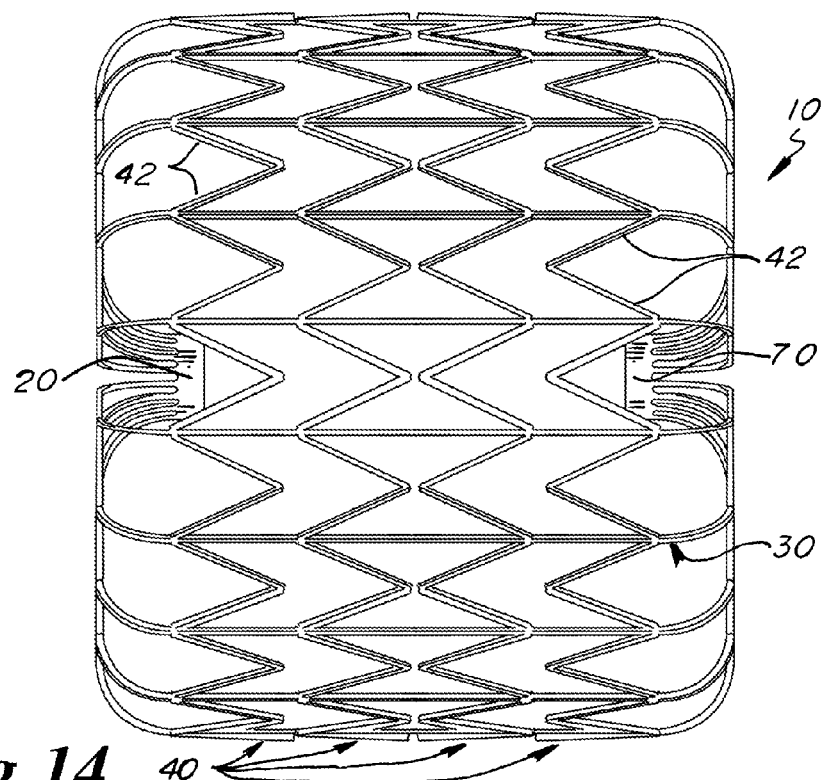
FIG. 14 is a side view of one or more embodiments of an expanded framework of the present disclosure having closed proximal and distal ends, wherein the ends are defined by an inverted proximal ring and an inverted distal ring.
Figure 15:
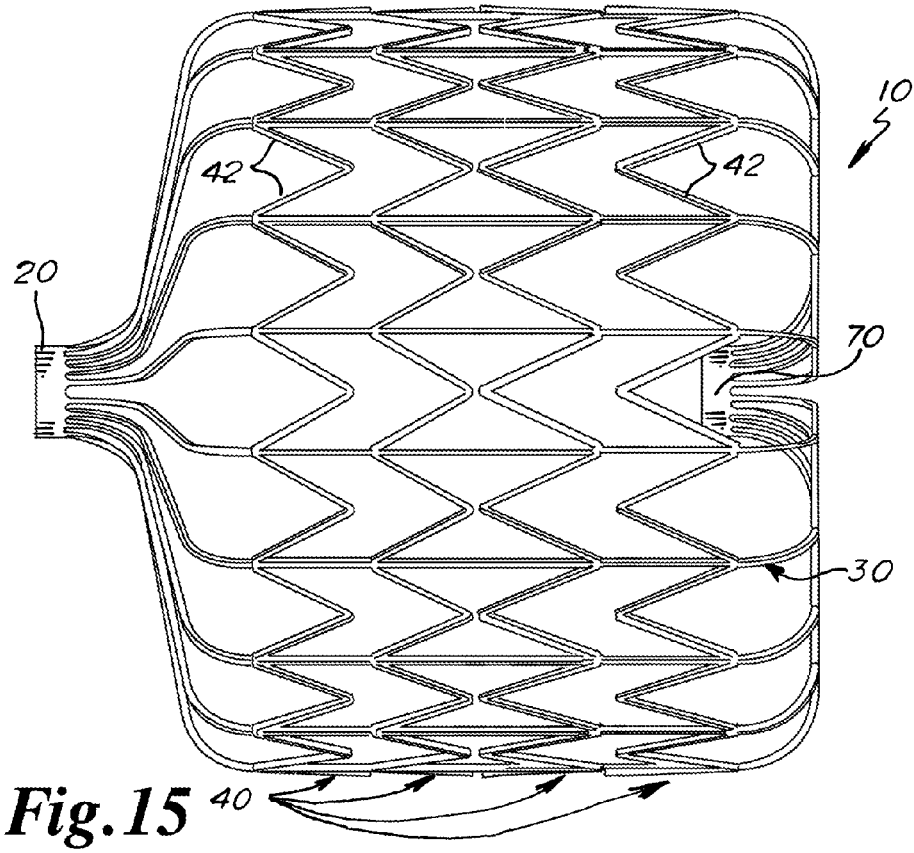
FIG. 15 is a side view of one or more embodiments of an expanded framework of the present disclosure having closed proximal and distal ends, wherein the ends are defined by an external proximal ring and an inverted distal ring (or vice versa).
Figure 16:
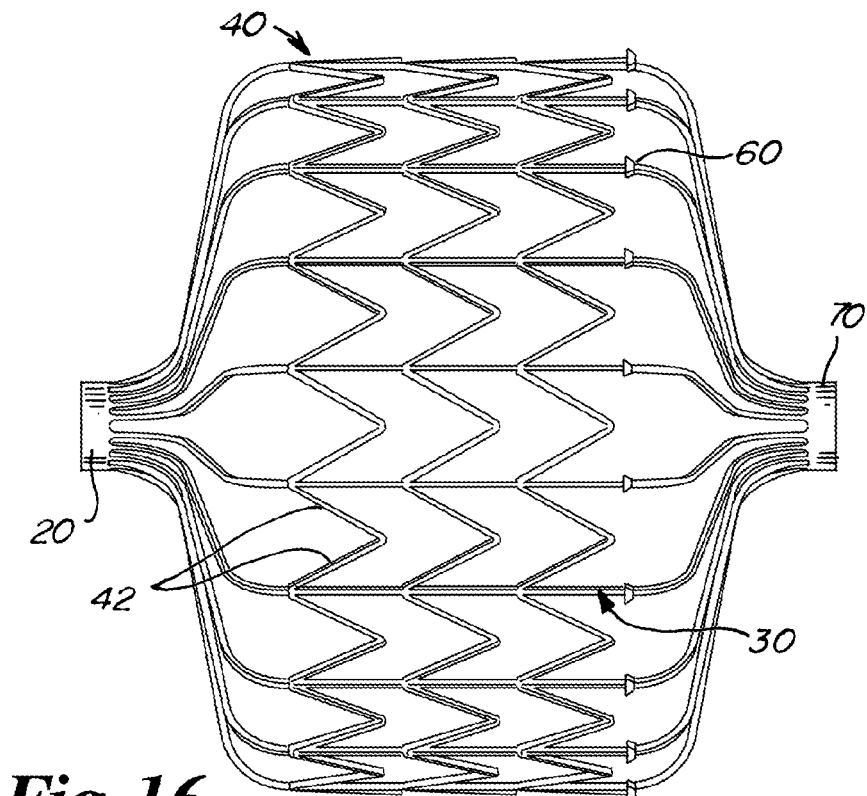
FIG. 16 is a side view of one or more embodiments of an expanded framework of the present disclosure having closed proximal and distal ends, wherein the end rings are both external and the beams near one end include securement anchors.

In some embodiments wherein the device is deployed or expanded, the framework 10 may include an open distal end and a first hub (e.g., a closed proximal end) (see, e.g., FIGS. 4-9). The first hub 20 (e.g., closed proximal end) may be defined by a proximal cap or ring from which the beams 30 may extend radially outward, as well as a predetermined distance longitudinally, to define the open distal end. In the embodiments of FIGS. 4-9, the proximal end of the framework 10 may be provided with a closed construction. The construction may be considered "closed" due to the presence of the first hub 20. The distal end 50 of the frameworks 10 of FIGS. 4-9, however, is open, in that the end column 40 of strut pairs 42, which extend from the distal ends 39 of the beams 30 are not secured to any other structure. In some embodiments, examples of which are shown in FIGS. 14-16, the framework 10 may be provided with a second hub (e.g., a closed construction distal end), whereby the beams 30 may extend longitudinally beyond the distal-most column 40 of strut pairs and turn radially inward toward a second hub 70, which may close the distal end of the structure in the same manner that the first hub closes the proximal end. In one or more embodiments, a plurality of beams 30 terminate at a second hub 70.

With reference to FIGS. 14-16, one or more embodiments of the present disclosure may include a framework including a plurality of beams that terminate at a second hub 70 (e.g., a distal cap or ring). In at least one embodiment the distal end of the framework may include a second hub (e.g., the end may be closed), such that the longitudinally extending beams 30 turn radially inward near the distal end of the device to a distal cap or ring.

In some embodiments, in a deployed or expanded state, the first hub 20 (e.g., proximal ring) may be longitudinally adjacent (external) to the entire length of the beams 30, such that the beams 30 extend longitudinally away from the first hub 20 in a single longitudinal (distal) direction (see FIGS. 4-6, 11, 12, and 15-17). In one or more embodiments, the first hub may be inverted (internal) such that the beams 30 initially extend in a first (proximal) longitudinal direction away from the first hub 20 and then as the beams turn and extend radially outward the beams curve back over the first hub 20 in the opposite (distal) longitudinal direction. In one or more embodiments wherein the device has a second hub 70 (e.g., a distal ring), the second hub 70 may be configured with an internal (see, e.g., FIGS. 14 and 15) or external configuration (see, e.g., FIG. 16). The internal or external positioning of the first hub 20 and second hub 70 may be the same or different. That is, in one or more embodiments, at least one of the first and second hubs may be inverted. For example, the first hub 20 and second hub 70 may be internally positioned (inverted) such as in the embodiment shown in FIG. 14. One hub (for example, first hub 20) may be externally positioned while the other hub (for example, second hub 70) may be inverted, such as in the embodiment depicted in FIG. 15.

With reference to FIGS. 14 and 15 having at least one inverted hub, at least a portion of the beams 30 may be J-shaped or C-shaped.

The physical characteristics of the strut pairs 42 may vary between the one or more embodiments of the framework 10. In some embodiments, each column 40 may have from ten to twenty strut pairs 42. The struts pairs may form angles (e.g., opening angles) between the struts in an expanded state of about 10 degrees to about 170 degrees (e.g., about 20 degrees to about 90 degrees, about 30 degrees to about 40 degrees etc.). In some embodiments the struts form angles in an expanded state below 45 degrees.

In the embodiment shown in, for example, FIG. 4, the length of each strut is substantially the same throughout the framework (which is not necessarily the case with all of the frameworks described herein, as is discussed herein). The lengths of the struts may be about 0.07 inch (about 1.77 mm) to about 0.20 inch (about 5.08 mm). The width of the struts can be about 0.003 inch (about 0.076 mm) to about 0.007 inch (about 0.177 mm). In the present disclosure, the widths of the struts may or may not be uniform throughout a column or throughout a framework.

In at least one embodiment, the framework 10 may have a fully expanded diameter of about 28 millimeters (mm). In one or more embodiments having such a diameter, each column 40 may have 18 strut pairs 42. The length of each strut may be about 0.15 inch (about 3.8 millimeters) and the width of each strut may be about 0.005 inch (about 0.127 millimeter).

In at least one embodiment, the framework 10 has a fully expanded diameter of about 20 millimeters. In one or more embodiments having such a diameter, each column 40 may have 18 strut pairs 42. The length of each strut may be about 0.10 inch (about 2.54 millimeters) and the width of each strut is about 0.005 inch (about 0.127 millimeter).

In embodiments wherein both the proximal end and distal end are closed (e.g., FIGS. 14-16), such as in the manner described herein, the columns 40 of strut pairs 42 may have a uniform orientation (all peaks "point" in the same direction) or, as in the embodiments shown in FIGS. 14 and 15 one or more columns 40 may have opposing orientations relative to one or more other columns. In still other embodiments, a framework 10 can include closed ends, and also include engagement anchors 60, such as in the example shown in FIG. 16.

Figure 17:
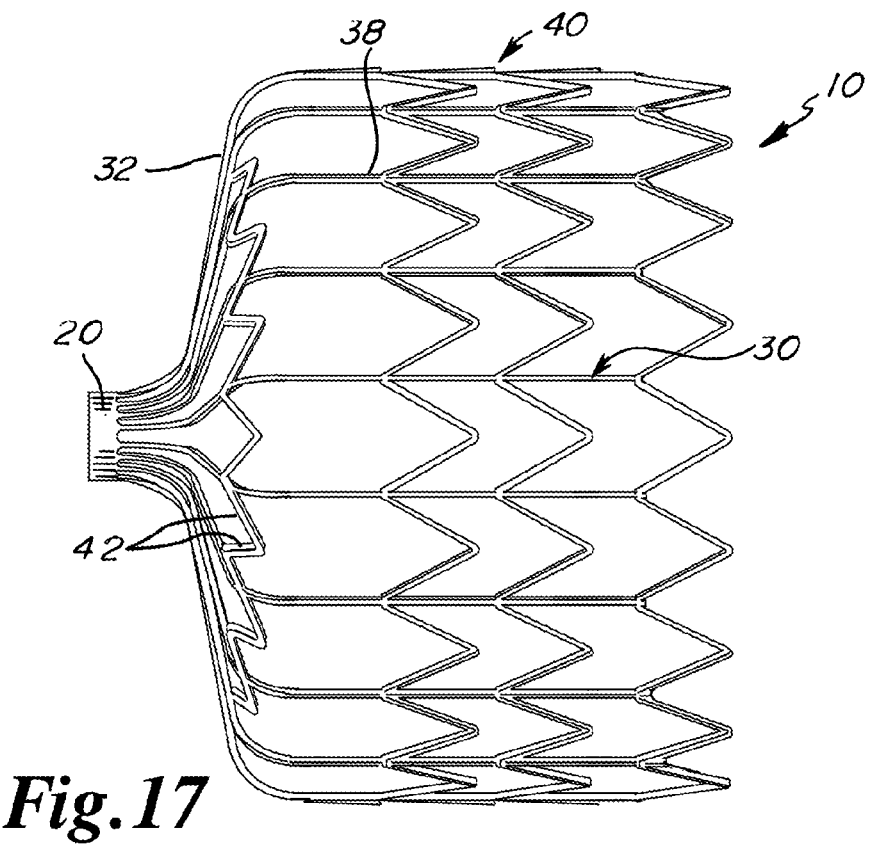
FIG. 17 is a side view of one or more embodiments of a framework of the present disclosure in an expanded state.

With reference to FIG. 17, in one or more embodiments, an occlusion device may include a circumferentially extending column 40 of strut pairs 42 connecting the first segments 32 and disposed between the first circumferentially extending column 40 of strut pairs 42 and the first hub 20. Such a configuration may provide additional structural support to the portion of the framework between the first circumferentially extending column 40 of strut pairs 42 and the first hub 20. The strut pairs 42 located between the first circumferentially extending column 40 of strut pairs 42 an first hub 20 are in addition to those strut pairs 42 which extend between only the second segments 38. While the strut pairs 42 that engage the first segments 32 of the beams 30 may be of similar construction as those which engage the second segments 38, in the embodiment depicted in FIG. 17, the strength of the proximally positioned strut pairs is less than the more distally positioned strut pairs (e.g., the strength of the proximally positioned strut pairs decreases as they move radially away from the center of the framework). This may provide increased resistance to circumferential bending and relative to the resistance at the maximum diameter. The differences in strength may be achieved by, for example, increasing the length of the struts (see, e.g., FIGS. 19 and 20) as the pattern moves away from the center axis. For example, the length of the struts connecting first segments 32 may be shorter than the length of the struts connecting second segments 38. In the one or more embodiments shown, the opening angle of the struts nearest the proximal ring 20 may be in a range of from 40 degrees to 80 degrees (e.g., approximately 80 degrees). In one or more embodiments, the opening angle may be outside this range.

Figure 18:
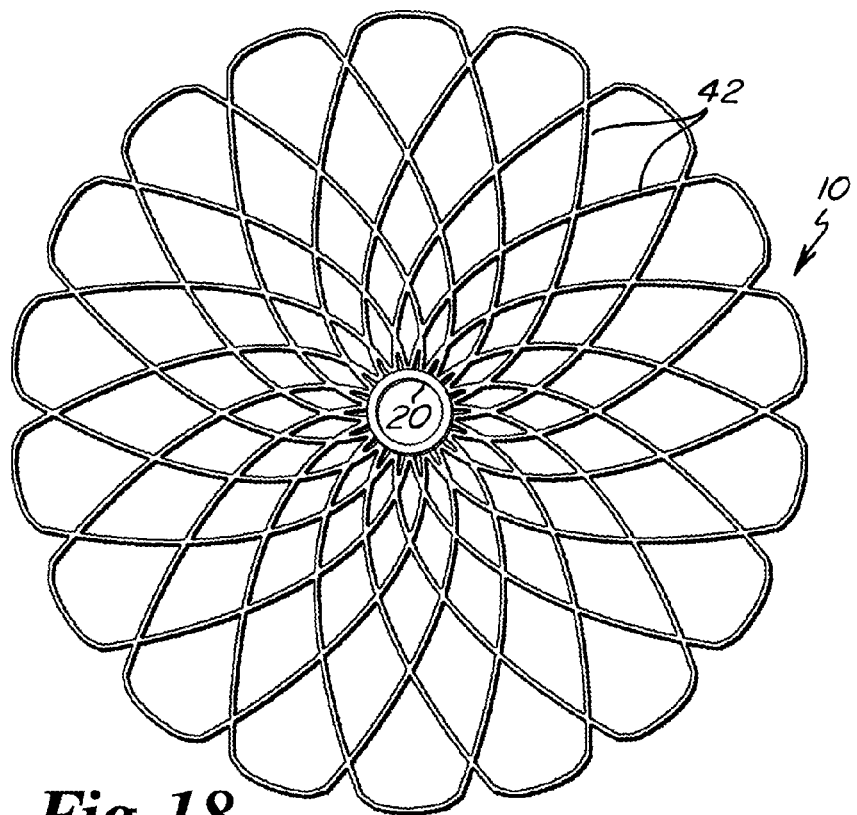
FIG. 18 is a front view of one or more embodiments of a framework of the present disclosure in an expanded state.
Figure 19:
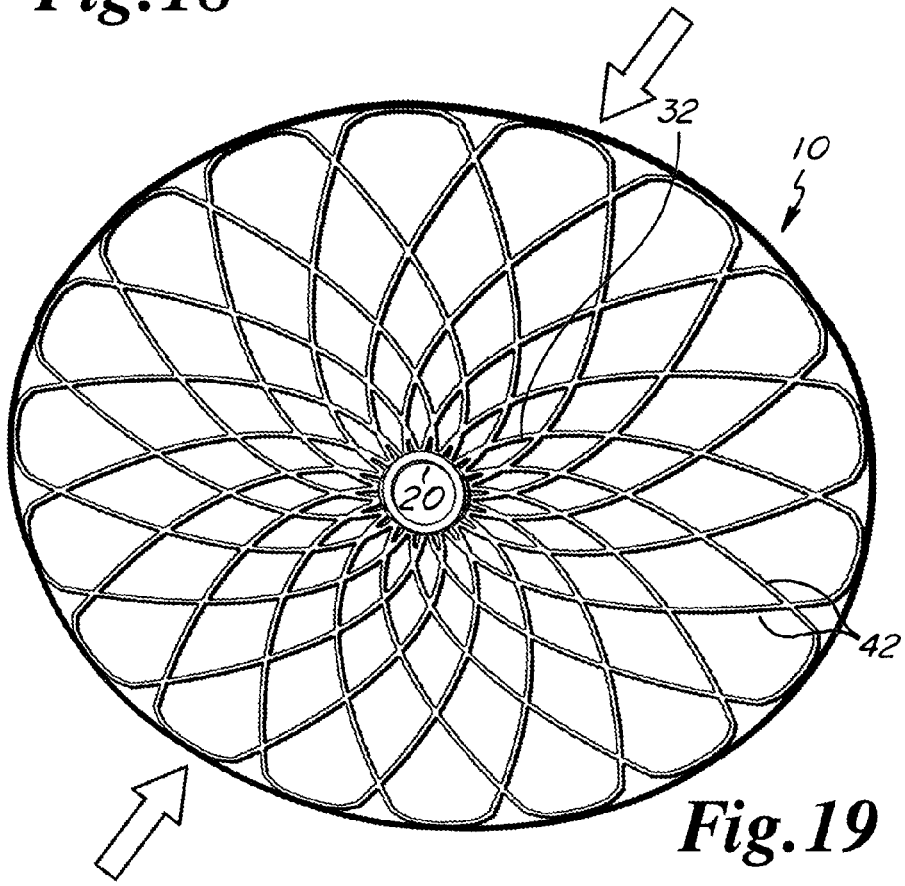
FIG. 19 is an illustration of one or more embodiments of the framework shown in FIG. 18 as it performs in the intended environment of use.

FIGS. 18 and 19 depict one or more embodiments similar to FIG. 17 in that the framework 10 includes strut pairs 42 connecting first segments 32 and/or connect radially extending segments, wherein the embodiments depicted in FIGS. 18 and 19 include an increased number of such strut pairs. In FIG. 18, the framework 10 is shown as expanded and is not constrained by exterior forces. In FIG. 19, the framework 10 is shown to have an increased resistance to distortion as a result of exterior forces applied. In one or more embodiments of the present disclosure, a framework 10 may be equipped with sufficient strength to support a filter or membrane, may have sufficient circumferential and/or radial strength to resist the distortive forces (indicated by arrows in FIG. 19) that the LAA exert on the occlusion device. As a result, the devices may form a seal with the interior wall of the LAA and may reduce or eliminate the amount of material that may exit the LAA and re-enter the blood stream. The regularity of the frameworks 10 of the present disclosure may also reduce the likelihood and/or severity of flattening during recapture of the device into a delivery catheter.

Figure 20:
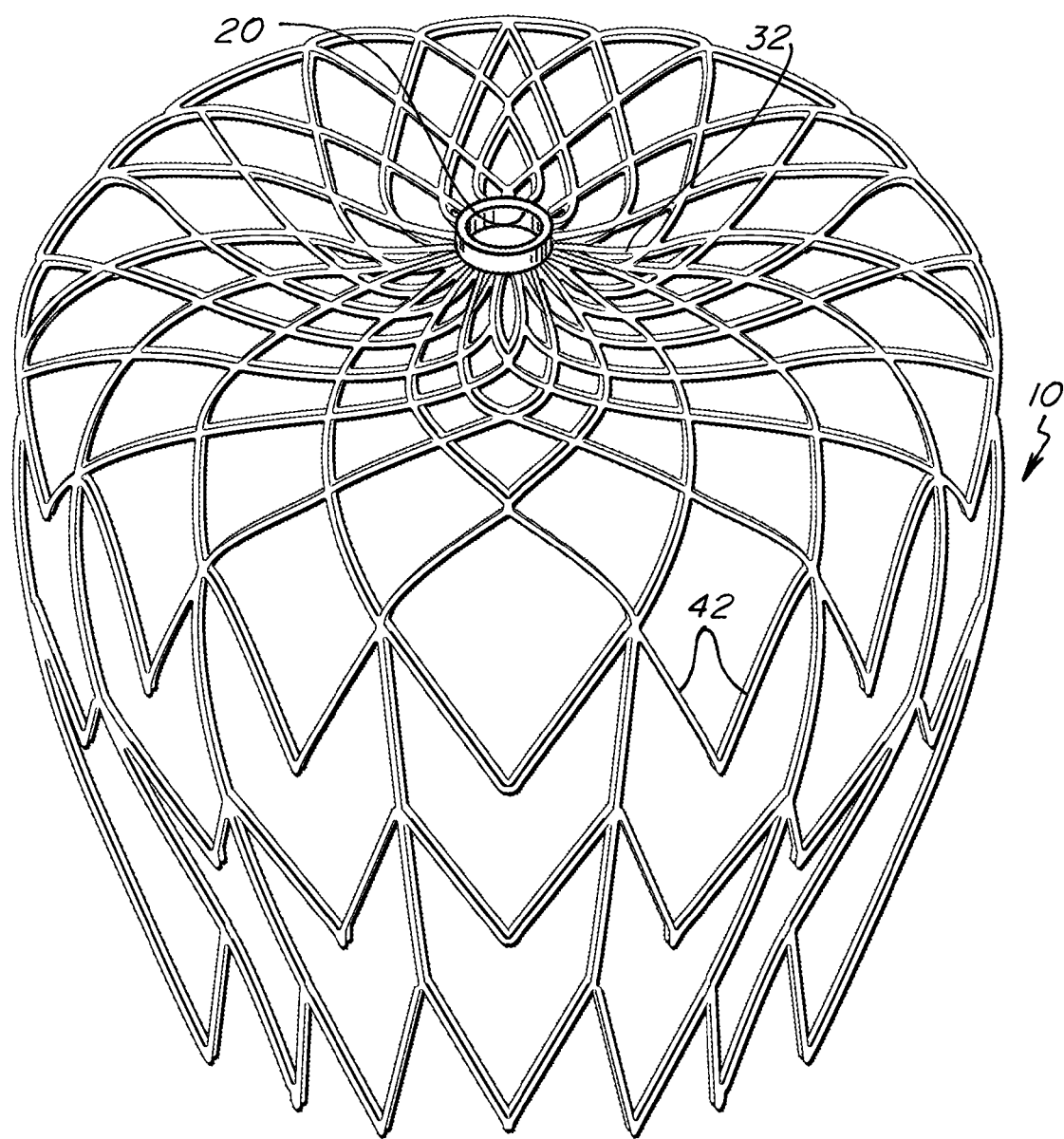
FIG. 20 is a schematic (proximal) end view of one or more embodiments of a framework similar to FIGS. 18-19.

FIG. 20 also depicts one or more embodiments similar to FIG. 17 (e.g., including strut pairs connecting first segments 32, etc.) and include portions of beams 30 that are not foreshortened (other than by, e.g., forming an exterior curve 37) upon moving from a first configuration to a second configuration. As discussed herein, the first hub 20 of FIG. 20 may, in one or more embodiments, take an exterior configuration or an inverted (interior) configuration.

In one or more embodiments, the covering may take any of a wide variety of forms known to one of skill in the art. For example, a covering may include a graft and/or a membrane and may include one or more layers. In one or more embodiments, a membrane or other covering may be disposed over and about most of the proximal end of framework 10. For example, a covering may be substantially bowl-shaped, with an opening that extends around the portion of the occlusion device having the greatest diameter in the second configuration. In the one or more embodiments that include anchors, the anchors 60 may penetrate the covering in both the first and second configurations (e.g., unexpanded and expanded states) to secure the covering on the framework 10. The covering may be any of a wide variety of biocompatible fabric, membrane, or material known to one of skill in the art. For example, the covering may be constructed of one or more layers of polyethylene terephthalate (PET). It should be recognized that the coverings described herein may be suitable for use with any of the embodiments of the framework 10 shown or described herein.

Other suitable covering materials may be employed as well. Examples may include, but are not limited to, polyethylene, polypropylene, polyvinyl chloride, polytetrafluoroethylene, including expanded polytetrafluoroethylene (ePTFE), fluorinated ethylene propylene, polyvinyl acetate, polystyrene, poly(ethylene terephthalate), naphthalene, dicarboxylate derivatives, such as polyethylene naphthalate, polybutylene naphthalate, polytrimethylene naphthalate, and trimethylenediol naphthalate, polyurethane, polyurea, silicone rubbers, polyamides, polyimides, polycarbonates, polyaldehydes, polyether ether ketone, natural rubbers, polyester copolymers, styrene-butadiene copolymers, polyethers, such as fully or partially halogenated polyethers, and copolymers and combinations thereof. See, for example, commonly assigned U.S. Pat. No. 8,114,147, the entire content of which is incorporated by reference herein.

As mentioned above, each of the various configurations of the framework 10 that have been shown and described herein may be deliverable from an unexpanded state (confined) to an expanded state or deployed state by a delivery system (e.g., a catheter). For example, a framework 10 in FIG. 21a is disposed within a delivery system, such as a catheter 100. In one or more embodiments, a plunger (not shown) may be used to apply an axial force in a distal direction on the collapsed framework 10 disposed within the catheter 100 so as to force the framework 10 from the catheter 100 (see FIG. 21b) and deploy it. In FIG. 21b, framework 10 is shown as partially deployed. As the entire framework is forced out of the catheter 100, the framework 10 may expand such that the second diameter may be greater than the diameter of first hub 20. The framework may be allowed to expand within a left atrial appendage (LAA). Any of a wide variety of delivery systems (e.g., catheters) may be suitable for use with the frameworks of the present disclosure. For example, suitable delivery systems may be disclosed in U.S. Pat. No. 6,994,092 to van der Burg et al.; U.S. Pat. Nos. 6,652,556 and 7,727,189 to VanTassel et al.

As previously mentioned, one or more embodiments of framework 10 (as well as the covering thereon) may be made from one or more of a wide variety of suitable biocompatible material including one or more polymers, one or more metals, or one or more combinations of polymer(s) and metal(s). Examples of suitable polymers may include, but are not limited to, expanded polytetrafluoroethylene (ePTFE) (e.g., Gortex®), polyester (e.g., Dacron®), polytetrafluoroethylene (PTFE) (e.g., Teflon), silicone, urethane, other biocompatible polymers, and blends, mixtures, or copolymers including one or more of these. In one or more embodiments, a framework may include metal fibers (e.g., in combination with a polymer). Examples of suitable metals may include, but are not limited to, stainless steel, titanium, tantalum, platinum, tungsten, gold and alloys of any of the above-mentioned metals. Examples of suitable alloys include, for example, platinum-iridium alloys, cobalt-chromium alloys including Elgiloy and Phynox, MP35N alloy, and nickel-titanium alloys, for example, nitinol. For example, in some embodiments the framework 10 may be constructed of or may include a flexible or super-elastic metal or alloy, such as, for example, nitinol. In at least one embodiment, the framework may be laser cut from a length of nitinol tubing. In one or more embodiments, a magnesium-based material may be used.

One or more embodiments of framework 10 may include (e.g., be made of) a shape memory material, such as super-elastic nitinol or spring steel, or may include one or more materials which may be plastically deformable. In the case of shape memory materials, the framework 10 may be provided with a memorized shape and then may be deformed to a reduced diameter shape. In one or more embodiments, the framework 10 may restore itself to its memorized shape upon, for example, being heated to a transition temperature and having any restraints removed therefrom. In at least one embodiment, the framework 10 is self-expanding to a pre-programmed expanded or deployed state.

One or more embodiments of framework 10 (e.g., those shown and described herein) may be created by methods including, but not limited to, cutting or etching a design from a tubular stock, from a flat sheet which is cut or etched and which is subsequently rolled, or from one or more interwoven wires or braids. Any other suitable technique which is known in the art or which is subsequently developed may also be used to manufacture one or more embodiments of the frameworks disclosed herein.

In some embodiments, it may be desirable to provide aspects of the framework 10 and/or covering with the ability to safely biodegrade over time. Thus, in some embodiments, the framework 10 and/or covering may be constructed from biodegradable materials that may also be biocompatible. By biodegradable, it is meant that a material will undergo breakdown or decomposition (e.g., into one or more substantially harmless compounds) as part of a biological process (e.g., a biological process one may anticipate may occur in the environment of an implantation site). In one or more embodiments, suitable polymers for the framework 10 and/or the covering may include polylactic acid, biodegradable polymers (e.g., biopolymers), injectable and biodegradable gels, poly(ethylene glycol) (PEG)/polyester, and magnesium-based material, and combinations of these.

In some embodiments, the framework 10, the delivery system (e.g., catheter 100), or another portion of the assembly may include one or more areas, bands, coatings, members, etc. that is (are) detectable by imaging modalities such as X-Ray, MRI, ultrasound, fluoroscopy, etc. In some embodiments, at least a portion of the framework 10 and/or adjacent assembly may be at least partially radiopaque (e.g., completely radiopaque).

In some embodiments, at least a portion of the framework 10 and/or covering may be configured to include one or more mechanisms for the delivery of a therapeutic agent. In one or more embodiments, the agent may be in the form of a coating or other layer (or layers) of material located or disposed on a surface region of the framework, wherein the therapeutic agent may be adapted to be released at the site of the framework's implantation and/or areas adjacent thereto. For example, in some embodiments at least a portion of the device is provided with one or more coatings of one or more therapeutic agents.

A therapeutic agent may be a drug or other pharmaceutical product such as non-genetic agents, genetic agents, cellular material, etc. Some examples of suitable non-genetic therapeutic agents include, but are not limited to: an anti-thrombogenic agent such as heparin, a heparin derivative, a vascular cell growth promoter, a growth factor inhibitor, paclitaxel, and combinations of two or more of these, etc. Where an agent includes a genetic therapeutic agent, such a genetic agent may include, but is not limited to: DNA, RNA, and their respective derivatives and/or components; a hedgehog protein, and combinations of two or more of these, etc. Where a therapeutic agent includes cellular material, the cellular material may include, but is not limited to: cells of human origin and/or non-human origin, as well as their respective components and/or derivatives thereof, and combinations of two or more of these. Where the therapeutic agent includes a polymer agent, the polymer agent may be, for example, a polystyrene-polyisobutylene-polystyrene triblock copolymer (SIBS), polyethylene oxide, silicone rubber, and/or any other suitable substrate, and combinations of two or more of these.

The above disclosure is intended to be illustrative and not exhaustive. This description will suggest many variations and alternatives to one of ordinary skill in this art. The various elements shown in the individual figures and described above may be combined or modified for combination as desired. Those skilled in the art may recognize other equivalents to the specific embodiment described herein which equivalents are intended to be encompassed by the claims attached hereto.

What is claimed is:

1. An occlusion device comprising:
   a framework comprising a proximal portion, a middle portion, and a distal portion, wherein:
   the proximal portion comprises a first hub that has a fixed first diameter;
   the middle portion has a second diameter and comprises a plurality of beams extending from the first hub to a distal portion, wherein each of the plurality of beams is connected to an adjacent beam by a first circumferentially extending column of strut pairs, and wherein the middle portion of the framework is movable between a first configuration wherein the second diameter is not greater than the first diameter and a second configuration wherein the second diameter is greater than the first diameter; and
   the distal portion has a third diameter, wherein the third diameter is not greater than the first diameter in the first configuration; and
   a biocompatible covering disposed over at least a part of the framework.

2. The occlusion device of claim 1, wherein each of the plurality of beams is connected to an adjacent beam by a second circumferentially extending column of strut pairs.

3. The occlusion device of claim 2, wherein each beam comprises:

a first segment extending from the first hub to the first circumferentially extending column of strut pairs; and a second segment extending from the first circumferentially extending column of strut pairs to the second circumferentially extending column of strut pairs.

4. The occlusion device of claim 3, wherein, upon moving from the first configuration to the second configuration, there is substantially no foreshortening of the second segment.

5. The occlusion device of claim 3, further comprising a third circumferentially extending column of strut pairs connecting the first segments and disposed between the first circumferentially extending column of strut pairs and the first hub.

6. The occlusion device of claim 1, wherein the framework is formed from a sheet.

7. The occlusion device of claim 1, wherein the first hub comprises a cap or a ring.

8. The occlusion device of claim 1, wherein the covering comprises a graft and/or a membrane.

9. The occlusion device of claim 1, wherein the first circumferentially extending column comprises at least two strut pairs having the same length.

10. The occlusion device of claim 1, wherein the framework further includes an anchor.

11. The occlusion device of claim 10, wherein the anchor extends from the middle portion through the covering.

12. The occlusion device of claim 1, wherein the plurality of beams terminate at a second hub.

13. The occlusion device of claim 12, wherein at least one of the first and second hubs is inverted.

14. The occlusion device of claim 1, wherein at least one of the plurality of beams is J-shaped or C-shaped.

15. An occlusion device comprising:

a framework comprising a proximal portion, a middle portion, and a distal portion, wherein:

the proximal portion comprises a first hub that has a fixed first diameter;

the middle portion has a second diameter and comprises a plurality of beams extending from the first hub to a distal portion, wherein each of the plurality of beams is connected to an adjacent beam by a first circumferentially extending column of strut pairs; and the distal portion has a third diameter; and a biocompatible covering disposed over at least a part of the framework; and wherein the framework further includes an anchor.

* * * * *